US012280100B2

(12) United States Patent
Singh et al.

(10) Patent No.: US 12,280,100 B2
(45) Date of Patent: Apr. 22, 2025

(54) VLP-BASED BIVALENT EBOLA VACCINES AND METHODS OF MAKING AND USING SAME

(71) Applicant: Children's Hospital Medical Center, Cincinnati, OH (US)

(72) Inventors: Karnail Singh, Deerfield Township, OH (US); Paul Spearman, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 18/392,463

(22) Filed: Dec. 21, 2023

(65) Prior Publication Data

US 2024/0131141 A1   Apr. 25, 2024

Related U.S. Application Data

(62) Division of application No. 17/411,097, filed on Aug. 25, 2021, now Pat. No. 11,890,337, which is a division of application No. 16/494,841, filed as application No. PCT/US2018/024747 on Mar. 28, 2018, now Pat. No. 11,129,886.

(60) Provisional application No. 62/477,480, filed on Mar. 28, 2017.

(51) Int. Cl.
| | |
|---|---|
| *C12N 7/00* | (2006.01) |
| *A61K 39/00* | (2006.01) |
| *A61K 39/12* | (2006.01) |
| *C07K 14/08* | (2006.01) |
| *C12N 15/113* | (2010.01) |
| *C12N 15/86* | (2006.01) |

(52) U.S. Cl.
CPC .............. *A61K 39/12* (2013.01); *C07K 14/08* (2013.01); *C12N 7/00* (2013.01); *A61K 2039/5258* (2013.01); *C12N 2740/10023* (2013.01); *C12N 2740/11023* (2013.01); *C12N 2740/12023* (2013.01); *C12N 2740/13023* (2013.01); *C12N 2740/14023* (2013.01); *C12N 2740/15023* (2013.01); *C12N 2740/16022* (2013.01); *C12N 2740/16023* (2013.01); *C12N 2760/14123* (2013.01); *C12N 2760/14134* (2013.01)

(58) Field of Classification Search
CPC ............ C12N 2740/11023; C12N 7/00; C12N 15/86; C12N 2740/11042; A61K 2039/5258
See application file for complete search history.

(56) References Cited

U.S. PATENT DOCUMENTS

| | | | |
|---|---|---|---|
| 9,045,727 B2 | 6/2015 | Compans et al. | |
| 9,597,388 B2 | 3/2017 | Weiner et al. | |
| 9,957,300 B2 | 5/2018 | Compans et al. | |
| 9,969,986 B2 | 5/2018 | Akahata et al. | |
| 11,129,886 B2 | 9/2021 | Singh et al. | |
| 11,890,337 B2 | 2/2024 | Singh et al. | |
| 2009/0210952 A1 | 8/2009 | Wu et al. | |
| 2010/0143406 A1 | 6/2010 | Smith et al. | |
| 2014/0004146 A1 | 1/2014 | Zhou et al. | |
| 2020/0085937 A1 | 3/2020 | Chen et al. | |

FOREIGN PATENT DOCUMENTS

| | | | |
|---|---|---|---|
| WO | WO 2015/066715 A1 | 5/2015 | |
| WO | WO 2016/168187 A1 | 10/2016 | |
| WO | WO 2017/015457 A1 | 1/2017 | |

OTHER PUBLICATIONS

Agnandji, S.T., et al., "Phase 1 Trials of rVSV Ebola Vaccine in Africa and Europe—Preliminary Report," N Engl J Med, Apr. 2016, 374(17):1647-1660, 22 pgs.

Falzarano, D., et al., "Single Immunization With a Monovalent Vesicular Stomatitis Virus—Based Vaccine Protects Nonhuman Primates Against Heterologous Challenge With *Bundibugyo ebolavirus*," JID, 2011, 204(Suppl 3):S1082-S1089, 8 pgs.

Grant-Klein, R.J., et al., "Condon-optimized filovirus DNA vaccines delivered by intramuscular electroporation protect cynomolgus macaques from lethal Ebola and Marburg virus challenges," Human Vaccines & Immunotherapeutics, 2015, 11:8, 15 pgs.

Henao-Restrepo, A.M., et al., "Efficacy and effectiveness of an rVSV-vectored vaccine expressing Ebola surface glycoprotein: interim results from the Guinea ring vaccination cluster-randomised trial," Lancet, 2015, 386:857-866, 10 pgs.

Huttner, A., et al., "The effect of dose on the safety and immunogenicity of the VSV Ebola candidate vaccine: a randomised double-blind, placebo-controlled phase 1/2 trial," Lancet Infect Dis, 2019, 15(10):1156-1166, 25 pgs.

Kibuuka, H., et al., "Safety and immunogenicity of Ebola virus and Marburg virus glycoprotein DNA vaccines assessed separately and concomitantly in healthy Ugandan adults: a phase 1b, randomised, double-blind, placebo-controlled clinical trial," Lancet, 2015, 385:1545-1554, 10 pgs.

(Continued)

*Primary Examiner* — Barry A Chestnut

(74) *Attorney, Agent, or Firm* — Frost Brown Todd LLP; Nicole M. Tepe

(57) ABSTRACT

Disclosed herein are virus-like particle (VLP)-based bivalent vaccine compositions. The compositions may comprise a spherical retroviral Group-specific Antigen ("Gag") protein core and at least two Ebola glycoproteins. The at least two Ebola glycoproteins may be located at the exterior surface of the spherical Gag protein core, such that the VLP-based vaccine presents at least two Ebola glycoprotein antigens. In one aspect, the at least two Ebola glycoproteins are a Zaire (EBOV) glycoprotein, and a Sudan (SUDV) glycoprotein.

14 Claims, 6 Drawing Sheets

Specification includes a Sequence Listing.

(56) References Cited

OTHER PUBLICATIONS

Kushnir, N., et al., "Virus-like particles as a highly efficient vaccine platform: Diversity of targets and production systems and advances in clinical development," Vaccine, 2012, 31:58-83, 26 pgs. XP055163741.

Ledgerwood, J.E., et al., "Chimpanzee Adenovirus Vector Ebola Vaccine—Preliminary Report," N Engl J Med, Nov. 2014, 60 pgs.

Ledgerwood, J.E., et al., "Chimpanzee Adenovirus Vector Ebola Vaccine," N Engl J Med, 2017, 376(10):928-938, 11 pgs.

Messaoudi, I., et al., "Filovirus pathogenesis and immune evasion: insights from Ebola virus and Marburg virus," Nat Rev Microbiol, Nov. 2015, 13(11):663-676, 30 pgs.

Rampling, T., et al., "A Monovalent Chimpanzee Adenovirus Ebola Vaccine—Preliminary Report," N Engl J Med, Jan. 2015, 10 pgs.

Singh, K., et al., "A Bivalent, Spherical Virus-Like Particle Vaccine Enhances Breadth of Immune Responses against Pathogenic Ebola Viruses in Rhesus Macaques," J Virol, 2020, 94(9):E01884-19, 19 pgs.

Singh, K., et al., "A novel Ebola virus antibody-dependent cell-mediated cytotoxicity (Ebola ADCC) Assay," Journal of Immunological Methods, 2018, 460:10-16, 7 pgs.
Stanley, D.A., et al., "Chimpanzee adenovirus vaccine generates acute and durable protective immunity against ebolavirus challenge," Nature Medicine, 2014, 20(10):1126-1129, 6 pgs.
Tapia, M.D., et al., "Use of ChAd3-EBO-Z Ebola virus vaccine in Malian and US adults, and boosting of Malian adults with MVA-BN-Filo: a phase 1, single-blind, randomised trial, a phase 1b, open-label and double-blind, dose-escalation trial, and a nested, randomised, double-blind, placebo-controlled trial," Lancet Infect Dis, 2016, 16(1):31-42, 12 pgs.
Warfield, K.L., et al., "Ebola Virus-Like Particle-Based Vaccine Protects Nonhuman Primates against Lethal Ebola Virus Challenge," The Journal of Infectious Diseases, 2007, 196(Suppl 2):S430-437, 8 pgs.
Warfield, K.L., et al., "Homologous and Heterologous Protection of Nonhuman Primates by Ebola and Sudan Virus-Like Particles," PloS One, 2015, 10(3):e0118881, 16 pgs.
Yonezawa, A., et al., "Studies of Ebola Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha," J Virol, 2005, 79(2):918-926, 9 pgs.
Zhu, F-C., et al., "Safety and immunogenicity of a novel recombinant adenovirus type-5 vector-based Ebola vaccine in healthy adults in China: preliminary report of a randomised, double-blind, placebo-controlled, phase 1 trial," Lancet, 2015, 385:2272-2279, 8 pgs.
European Search Report, Extended, and Written Opinion dated Dec. 16, 2020 for Application No. EP 18776312.3, 25 pgs.
European Search Report, Extended, and Written Opinion dated Dec. 16, 2020 for Application No. EP 18778205.7, 24 pgs.
International Search Report and Written Opinion dated Jun. 14, 2018 for Application No. PCT/US2018/024747, 14 pgs.
International Search Report and Written Opinion dated Aug. 28, 2018 for Application No. PCT/US2018/024758, 11 pgs.

VLP-BASED BIVALENT EBOLA VACCINES AND METHODS OF MAKING AND USING SAME

CROSS-REFERENCE TO RELATED APPLICATIONS

This application claims priority to and benefit of 62/477,480, entitled "Development and Evaluation of a Novel Bivalent Virus Like Particle (VLP) based Ebola Vaccine" filed Mar. 28, 2017, the contents of which are incorporated in its entirety for all purposes.

REFERENCE TO SEQUENCE LISTING

A Sequence Listing submitted as an XML text file via EFS-WEB is hereby incorporated by reference. The name of the XML file for the Sequence Listing is 20170207b3a1_ST26_01092024.xml, the date of the creation of the XML file is Jan. 9, 2024, and the size of the XML file is 10,188 bytes.

BACKGROUND

Ebolaviruses have caused epidemics in humans that are characterized by high mortality rates. The 2013-2016 Ebolavirus epidemic in West Africa resulted in more than 28,600 infections and 11,300 deaths (WHO June 2016). The extent of the outbreak coupled with a high rate of mortality emphasized the importance of developing new therapeutics and preventive vaccines against Ebolaviruses. Several candidate Ebola vaccines have shown protection in the non-human primate (NHP) model of Ebola. Three of the most promising live attenuated vaccines for Ebola are those derived from Vesicular stomatitis virus (VSV), Chimp Adenovirus Type 3 (ChAd3), and Modified Vaccinia Ankara (MVA). However, none of these approaches has proven capable of eliciting long-lasting protective immune responses.

Successful development of a vaccine will significantly help in the prevention and control of Ebola epidemics in Africa as well as protect health-care workers and researchers working with these deadly viruses. Such a vaccine will also be extremely useful in the event of a bio-terrorism attack and protecting American troops abroad. Clinical care of Ebola infected patients needs special infrastructure, restricted-access facilities and highly trained health-care workers and there is a very high cost associated with this. Thus, the economic impact of developing such a vaccine also cannot be underestimated. The instant disclosure addresses one or more of the aforementioned needs in the art.

BRIEF SUMMARY

Disclosed herein are virus-like particle (VLP)-based bivalent vaccine compositions. The compositions may comprise a spherical retroviral Group-specific Antigen ("Gag") protein core and at least two Ebola glycoproteins. The at least two Ebola glycoproteins may be located at the exterior surface of the spherical Gag protein core, such that the VLP-based vaccine presents at least two Ebola glycoprotein antigens. In one aspect, the at least two Ebola glycoproteins are a Zaire (EBOV) glycoprotein, and a Sudan (SUDV) glycoprotein.

BRIEF DESCRIPTION OF THE DRAWINGS

Those of skill in the art will understand that the drawings, described below, are for illustrative purposes only. The drawings are not intended to limit the scope of the present teachings in any way.

Figure 1:
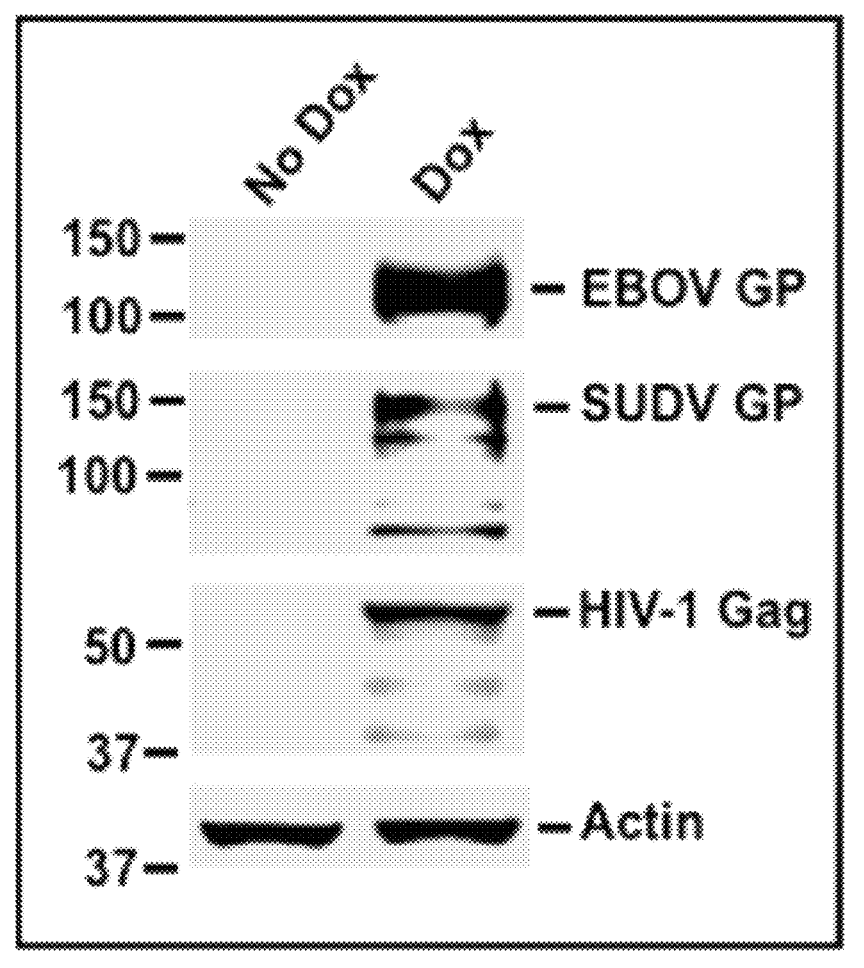

FIG. 1. Inducible expression of EBOV GP, SUDV GP and HIV-1 Gag in ESGPGag 293F cells. Cells were cultured as such or induced with Dox for 24 h and cell lysates probed by western blotting for EBOV GP, SUDV GP, HIV-1 Gag and actin using specific antibodies.

Figure 2:
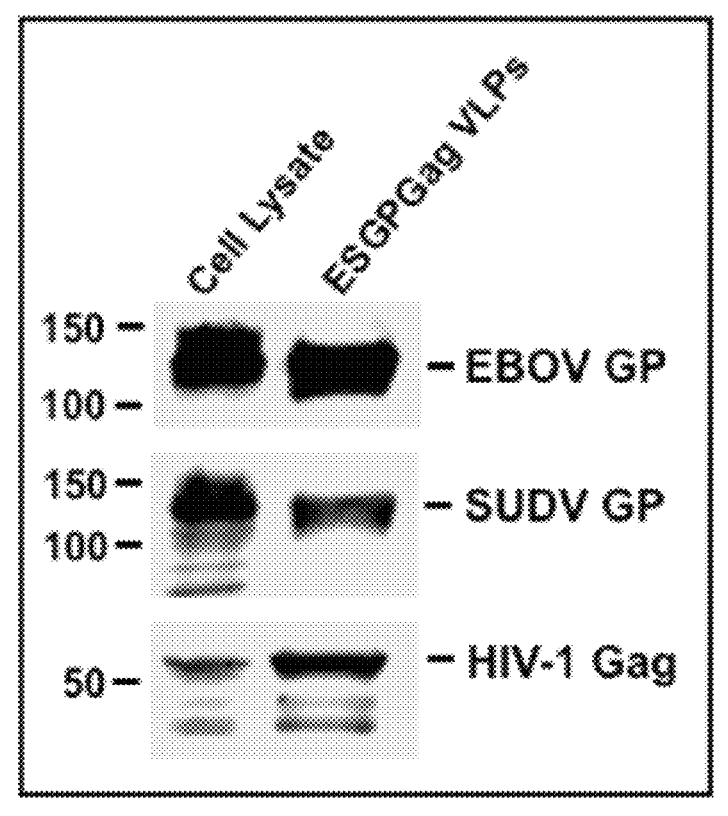

FIG. 2. Dox induced secretion of ESGPGag VLPs containing EBOV GP, SUDV GP and HIV-1 Gag by ESGPGag 293F cells. Supernatant from cells induced with Dox was layered on 20% sucrose cushion and subjected to ultracentrifugation. VLP pellets so obtained and the cell lysates were probed by western blotting using anti-EBOV GP, anti-SUDV GP and anti-HIV-1 Gag specific antibodies.

Figure 3:
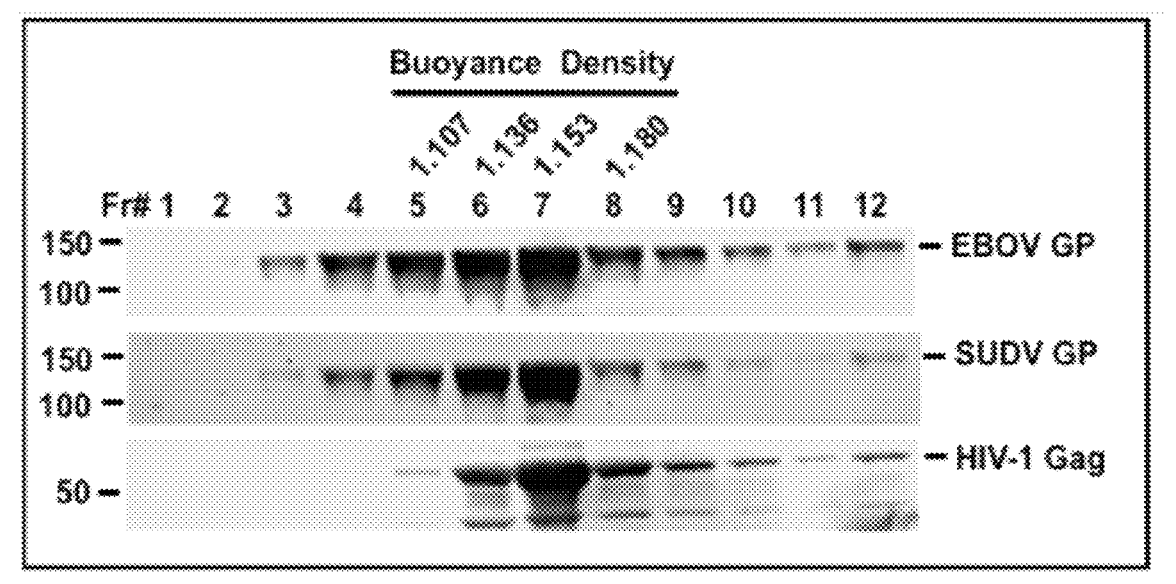

FIG. 3. Buoyance density analysis of ESGPGag VLPs. Fractions collected after ultracentrifugation of ESGPGag VLPs over 20-60% sucrose gradient were probed by western blotting using anti-EBOV GP, anti-SUDV GP and anti-HIV-1 Gag specific antibodies. Buoyance density of each fraction was determined by using a refractometer. ESGPGag VLPs were found to have a buoyance density between 1.136-1.180 with the peak at 1.153

Figure 4:
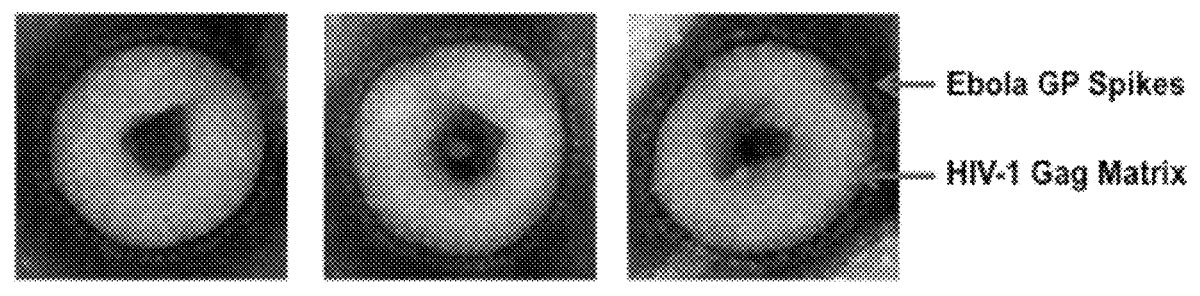

FIG. 4. Negative electron microscopy of ESGPGag VLPs. VLPs harvested from culture supernatants after ultracentrifugation on 20% sucrose cushion were analyzed by negative electron microscopy. The analysis showed spherical particles abundantly covered with spikes of glycoproteins on their surface.

FIG. 5. Immunoreactivity of rabbit anti-ESGPGag VLP sera with recombinant Ebola glycoproteins. Elisa plates were coated with 20 ng/well of either recombinant EBOV GPdTM or SUDV GPdTM proteins, blocked and incubated with increasing dilutions of rabbit anti-ESGPGag VLP sera. Protein bound antibodies were detected by incubating the wells with horse radish peroxidase (HRP) bound anti-rabbit IgG detecting antibodies followed by the addition of HRP substrate and measuring the optical density at 450 nm.

FIG. 6. Rabbit anti-ESGPGag VLP sera strongly neutralize all four species of Ebolavirus pathogenic to humans. EBOV, SUDV, BDBV, TAFV and MARV GP containing HIV-1ΔEnv pseudovirions were incubated with different dilutions of rabbit anti-ESGPGag VLP sera for one hour and then added onto TZM-bl cells that express luciferase under the control of HIV-1 Tat. 48 hours later luciferase activity was measured and percentage neutralization calculated by comparing luciferase activity in the test wells to that in the wells that received respective pseudovirions that was not incubated with any antibody/serum.

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some embodiments, the terms refer to humans. In further embodiments, the terms may refer to children.

Ebola virus disease (EVD) is caused by Ebola viruses that are filamentous, negative-strand RNA viruses belonging to the family Filoviridae. There are five species of the Ebola viruses; Zaire ebolavirus (EBOV), Sudan ebolavirus (SUDV), Bundibugiyo ebolavirus (BDBV), Tai-forest ebolavirus (TAFV) and Reston ebolavirus (RESTV). First four have been shown to be pathogenic in humans whereas RESTV has been shown to cause disease only in non-human primates. Ebolavirus structure consists of an inner nucleocapsid made up of nucleoprotein (NP) and containing the viral RNA, along with RNA polymerase L, transcription factor VP30 and cofactor VP35. The viral nucleocapsid is surrounded by a lipid bilayer that contains the envelope protein spikes of glycoprotein (GP). Between the viral envelope and nucleocapsid are the matrix proteins VP40 and VP24 (1). Because of its integral role in the pathogenesis of EVD, GP has been the relevant target of all the candidate Ebola vaccines developed so far.

A number of candidate Ebola vaccines have been developed and evaluated in non-human primate (NHP) model of EVD as well as in clinical trials (2-11). A few of them were fast tracked to the clinical trials during the 2013-2016 Ebola epidemic. Ebola vaccines such as the vesicular stomatitis virus (VSV), adenovirus 5 (Ad5) or chimpanzee adenovirus 3 (ChAd3)-vectored vaccines appear quite promising in generating protective immune responses. However, each candidate has substantial limitations. For example, the VSV vaccine elicits a high rate of adverse events so that acceptability for licensure remains in doubt (2, 3) Recombinant human adenoviral vectored vaccines are limited by pre-existing immunity to the vector in the human populations at risk for Ebola (4). Chimpanzee adenovirus based Ebola vaccine like ChAd3-EBO and ChAd3-EBO-Z have been developed to bypass the pre-existing immunity to the vector in the humans. However, in non-human primate models of Ebola virus disease (EVD), these vaccines did not induce durable protective immunity (11). Boosting of animals after priming with this vaccine with Modified Vaccinia Ankara (MVA)-Filo vaccine that has glycoproteins (GP) from Zaire (EBOV), Sudan (SUDV) and Marburg (MARV) viruses and nucleoprotein from Tai-Forest (TAFV) virus has been shown to extend the duration of protective immune responses against lethal EBOV challenge (11). Together these studies clearly suggested that novel Ebola vaccines, that either alone or in combination with other vaccines, are needed that can provide long-term protective immunity against the dreadful Ebolaviruses.

Disclosed herein is the successful development and production of a novel virus-like particle (VLP) based bivalent Ebola vaccine that expresses Ebola glycoproteins (GP) from Zaire (EBOV) and Sudan (SUDV) species on the HIV-1 Gag core. The immunogenicity of this dual-glycoprotein VLP Ebola vaccine and its ability to generate high titers of functional neutralizing antibodies was tested by immunizing rabbits with this vaccine combined with adjuvants Poly (I:C) and CpG. Immunization of rabbits produced high titered binding anti-EBOV GP and anti-SUDV GP antibodies that neutralized all four pathogenic species of Ebolavirus. This VLP-based vaccine product is an ideal reagent to employ either as a stand-alone Ebola vaccine or in combination (prime-boost) with other experimental Ebola vaccines and has high commercial potential.

The disclosed VLP platform may be used for large-scale production of a nanoparticle bivalent Ebola vaccine. The production system is based on a stable and inducible ESGP-Gag 293F cell line that, upon induction with doxycycline (Dox), secretes VLPs with HIV-1 Gag core abundantly studded with Ebola glycoproteins (GPs) from Zaire (EBOV) and Sudan (SUDV) Ebolaviruses. The Gag core provides a very stable framework of ~110 nm on which Ebola GPs are incorporated in their native conformation. Initial immunogenicity results in rabbits are highly promising, with high binding titers and substantial neutralization elicited against all the four pathogenic Ebolavirus species. There are several unique aspects of this VLP approach. (1) The ESGPGag 293F stable cell production system can be easily scaled up to produce large quantities of clinical grade Ebola VLPs. (2) The spherical Gag core exhibits enhanced stability as compared with other framework constructs such as Ebola VP40 protein. (3) The VLP-based vaccines are non-infectious, have antigen in stable and native conformation, and do not suffer from the limitation of pre-existing immunity. This bivalent Ebola vaccine may provide protection as a stand-alone vaccine, or may be even more advantageous when provided as a booster vaccine following priming with other experimental Ebola vaccines.

Disclosed herein are virus-like particle (VLP)-based bivalent vaccine compositions. The compositions may comprise a spherical retroviral Group-specific Antigen ("Gag") protein core and at least two Ebola glycoproteins. The at least two Ebola glycoproteins may be located at the exterior surface of the spherical Gag protein core, such that the VLP-based vaccine presents at least two Ebola glycoprotein antigens. In one aspect, the at least two Ebola glycoproteins are a Zaire (EBOV) glycoprotein, and a Sudan (SUDV) glycoprotein. SUDV is described as YP 138523.1 in the literature, whereas an example of EBOV GP is reported as NCBI Reference Sequence: NP 066246.1, both incorporated herein in their entirety by reference. An exemplary Gag protein includes, but is not limited to, that of SEQ ID NO: 1. Exemplary glycoproteins include, but are not limited to, those set forth in SEQ ID NOS 2, 3, and 4. It will be understood by one of ordinary skill in the art that one may employ a sequence having at least 50%, 60%, 70%, 75%, 80%, 85%, 90%, 95%, 96%, 97%, 98%, 99%, or 100% identity to the reference sequence, which may include the sequences disclosed herein or as otherwise known in the art. The length of comparison sequences may be at least 5 contiguous nucleotides or amino acids, or at least 10, 11, 12, 13, 14, 15, 16, 17, 18, 19, 20, 21, 22, 23, 24, or 25 contiguous nucleotides or amino acids, or the full-length nucleotide or amino acid sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

In one aspect, the Gag protein may be derived from a retrovirus. For example, suitable retroviruses from which the gag protein may be derived include human immunodeficiency virus (HIV), murine leukemia virus (MLV) Rous sarcoma virus (RSV), Equine infectious anemia virus (EIAV), or the like. The sequences of such will be readily appreciated by one of ordinary skill in the art.

In one aspect, it has been surprisingly found that the glycoproteins are capable of aggregating at a relatively high density at the surface of the spherical gag core. In certain aspects, the EBOV GP Concentration may be about 20 to about 60 ug/ml, or about 20 to about 50 ug/ml, for example, in one aspect, 22-50 ug/ml. The SUDV GP Concentration may be about 1 to about 15 ug/ml, or about 2 to about 12 ug/ml, or, for example, in one aspect, 3 to 11 ug/ml. The HIV-1 Gag Concentration may be about 2 to about 20 ug/ml, or about 3 to about 18 ug/ml, or for example, in one aspect, 4 to 15 ug/ml. The concentrations of EBOV GP and SUDV GP, may be measured by semi-quantitative western blotting using known quantities of purified recombinant EBOV GP and SUDV GP respectively. Concentrations of HIV-1 Gag VLPs may be measured by an HIV-1 Gag specific ELISA using known quantities of purified HIV-1 Gag. In one aspect, the spherical Gag protein core may have a diameter of from about 100 to about 300 nanometers.

In one aspect, the VLP composition, while containing only the EBOV and SUDV glycoproteins, may be sufficient to immunize an individual against a viral infection from one or more of Zaire (EBOV), Sudan (SUDV), Bundibugyo (BDBV) and Tai Forest (TAFV), or in some aspects, two or more of Zaire (EBOV), Sudan (SUDV), Bundibugyo (BDBV) and Tai Forest (TAFV), or three or more of Zaire (EBOV), Sudan (SUDV), Bundibugyo (BDBV) and Tai Forest (TAFV), or all four of Zaire (EBOV), Sudan (SUDV), Bundibugyo (BDBV) and Tai Forest (TAFV).

The disclosed compositions may further comprise one or more pharmaceutical-acceptable carriers, which may include any and all solvents, dispersion media, coatings, stabilizing agents, diluents, preservatives, antibacterial and antifungal agents, isotonic agents, adsorption delaying agents, and the like. The disclosed S particles may be provided in physiological saline. Optionally, a protectant may be included, for example, an anti-microbiological active agent, such as for example Gentamycin, Merthiolate, and the like. The compositions may further include a stabilizing agent, such as for example saccharides, trehalose, mannitol, saccharose and the like, to increase and/or maintain product shelf-life. Those of skill in the art will understand that the composition herein may incorporate known injectable, physiologically acceptable sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants will be appreciated by one of ordinary skill in the art.

In one aspect, disclosed is a container comprising at least one dose of the immunogenic compositions disclosed herein. The container may comprise 1 to 250 doses of the immunogenic composition, or in other aspects, 1, 10, 25, 50, 100, 150, 200, or 250 doses of the immunogenic composition. In one aspect, each of the containers may comprise more than one dose of the immunogenic composition and may further comprises an anti-microbiological active agent. Those agents may include, for example, antibiotics such as Gentamicin and Merthiolate and the like.

A further aspect relates to a kit. The kit may comprise any of the containers described above and an instruction manual, including the information for the delivery of the immunogenic composition disclosed above. For example, instructions related to intramuscular application of at least one dose may be provided for lessening the severity of clinical symptoms associated with an infection of an antigen as disclosed here. The kits and/or compositions may further include an immune stimulant such as keyhole limpet hemocyanin (KLH), or incomplete Freund's adjuvant (KLH/ICFA). Any other immune stimulant known to a person skilled in the art may also be used.

In one aspect, a method for eliciting an immune response an individual in need thereof against an Ebola virus species selected from Zaire (EBOV), Sudan (SUDV), Bundibugyo (BDBV), Tai Forest (TAFV), and combinations thereof is disclosed. The method may comprise the step of administering a composition as disclosed herein. In this aspect, the method may include the step of administering a vaccine composition as disclosed above to an individual in need thereof. It will be readily appreciated that the disclosed compositions may be administered to an individual according to any method known in the art, and that optimal administration (including route and amounts) will not require undue experimentation. The vaccine compositions may be administered prophylactically to an individual suspected of having a future exposure to the antigen incorporated into the vaccine composition. In certain aspects, provided is a method of providing an immune response that protects an individual receiving the composition from infection, or reduces or lessens the severity of the clinical symptoms associated from an Ebola infection. Dosage regimen may be a single dose schedule or a multiple dose schedule (e.g., including booster doses) with a unit dosage form of the composition administered at different times. The term "unit dosage form," as used herein, refers to physically discrete units suitable as unitary dosages for human and animal subjects, each unit containing a predetermined quantity of the antigenic compositions disclosed herein in an amount sufficient to produce the desired effect, which compositions are provided in association with a pharmaceutically acceptable excipient (e.g., pharmaceutically acceptable diluent, carrier or vehicle). The vaccine may be administered in conjunction with other immunoregulatory agents.

The dosage regimen may take a variety of different forms. For example, the individual may be administered a first dose of the disclosed composition followed by a second dose of the composition. In certain aspects, the second dose may be administered at a second point in time selected from a day after the first dose, a week after the first dose, two weeks after the first dose, three weeks after the first dose, and four weeks after the first dose.

In one aspect, a method of making the bivalent VLP compositions is disclosed. The method may comprise the steps of purifying from a cell line culture a VLP composition comprising a spherical retroviral Group-specific Antigen ("Gag") protein core and at least two Ebola glycoproteins, wherein said at least two Ebola glycoproteins are incorporated into the surface of the spherical Gag protein core. The cell line may be stably transfected with a first plasmid containing a gag sequence under the control of an inducible promoter, a second plasmid containing an Ebola glycoprotein sequence under the control of an inducible promoter, and a third plasmid containing an Ebola glycoprotein sequence under the control of an inducible promoter. the second and third plasmid may contain different Ebola glycoproteins. The stably transfected cell line may produce the spherical Gag protein core and the at least two Ebola glycoproteins. The at least two Ebola glycoproteins self-assemble at the surface of said spherical Gag protein core. The first plasmid, second plasmid, and third plasmid may be antibiotic resistant. This antibiotic resistance allows the cells stably transfected with the three plasmids to grow in a selection media containing the three antibiotics.

In one aspect, the stably transfected cell line may produce the Gag protein core upon induction with doxycycline. The VLP produced by the cell lines may be purified by ultracentrifugation. The purification may be via a sucrose cushion, such as, for example a 20% sucrose cushion, or by cross-flow filtration followed by ultracentrifugation.

In one aspect, the cell line may be a human cell line modified to stably express Gag, EBOV GP, and SUDV GP under inducible promoters. In one aspect, the cell line may be a 293F cell line, in a further aspect, the cell line may be a 293F 6/TR cell line In one aspect, a cell line comprising a first plasmid containing a sequence encoding for a gag protein under the control of an inducible promoter, a second plasmid containing a sequence encoding for a first Ebola glycoprotein under the control of an inducible promoter, and a third plasmid containing a sequence encoding for a second Ebola glycoprotein under the control of an inducible promoter is disclosed. The Ebola glycoprotein may be Zaire (EBOV). The cell line may further contain a third plasmid containing a sequence encoding for a second Ebola glycoprotein under the control of an inducible promoter, wherein the second Ebola glycoprotein is SUDV. In one aspect, the cell line may be a human cell line modified to stably express Gag, EBOV GP, and SUDV GP under inducible promoters. In one aspect, the cell line may be a 293F cell line, in a further aspect, the cell line may be a 293F 6/TR cell line the cell line may be stably transfected with the plasmids. In certain aspects, the cell line may be an inducible cell line. Any of the aforementioned sequences may be codon-optimized. Codon optimization is readily understood by one of ordinary skill in the art, described, for example, at www.idtdna.com/CodonOpt

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Methods

Plasmids. The HIV-1 Gag gene was introduced between HindIII and BamHI sites of plasmid pcDNA4/TO (Invitrogen, Carlsbad, CA) to generate plasmid pcDNA4/TO HIV-1 Gag. pcDNA5/TO-puro and pcDNA5/TO-neo plasmids were created by replacing hygromycin resistance gene sequence of original pcDNA5/TO vector (Invitrogen, Carlsbad, CA) with a puromycin and neomycin resistance genes, respectively. Briefly, the puromycin or neomycin resistance gene was amplified by polymerase chain reaction (PCR). The hygromycin resistance gene was deleted from the original pcDNA5/TO plasmid by digestion with enzyme Pml I, and the puromycin or neomycin resistance gene inserted in its place. The sequence and orientation of the inserts were verified. Codon-optimized EBOV GP Mayinga gene was synthesized by GenScript (Piscataway, NJ) and placed under a tetracycline-controlled cytomegalovirus (CMV) promoter into plasmid pcDNA5/TO-puro using BamHI and EcoRI sites to generate the plasmid pcDNA5/TO-puro EBOV GP. Codon-optimized SUDV GP Gulu gene was purchased from Sino-Biological (Beijing, China) and placed under a tetracycline-controlled cytomegalovirus (CMV) promoter into plasmid pcDNA5/TO-neo using HindIII and XbaI sites to generate the plasmid pcDNA5/TO-neo SUDV GP.

Development of stably transfected ESGPGag 293F cells with inducible expression of EBOV GP, SUDV GP and HIV-1 Gag: 293F cells, cultured in 293 Expression Media supplemented with 5 µg/ml blasticidin (Invivogen, San Diego, CA), were transfected with pcDNA4/TO HIV-1 Gag, pcDNA5/TO-puro EBOV GP and pcDNA5/TO-neo SUDV GP together using Lipofectamine 2000. Forty-eight hours later, the cells were washed and transferred into the selection media (293 Expression Media supplemented with 5 µg/ml blasticidin, 10 µg/ml Zeocin (Invivogen), 1.0 µg/ml puromycin (Invivogen) and 500 µg/ml G418 (Invivogen)). Cells were selected and expanded over the coming weeks till their number reached ~10×10$^6$. A part of the cells was harvested and aliquots cryopreserved in liquid nitrogen. Remaining cells were continued in the cultured and then either left untreated or induced with Dox (2 µg/ml) (Sigma-Aldrich) for 24 hours, cells harvested and cell lysates tested for EBOV GP, SUDV GP and HIV-1 Gag expression by western blotting using specific antibodies. Cell cultures with high EBOV GP, SUDV GP and HIV-1 Gag expression were selected and labeled ESGPGag 293F cells, expanded and selected for further work. Multiple aliquots of these cells were cryopreserved in liquid nitrogen.

Analysis of ESGPGag VLPs secreted by ESGPGag 293F cells upon induction with Dox: ESGPGag 293F cells were cultured in 293 Expression Media in Erlenmeyer flasks to a density of 1.5×106 cells per ml and cultures induced with Dox (2 µg/ml). 40 hours later, cells and supernatants were separated by high-speed centrifugation. Harvested cells were lysed and cell lysates frozen in −80° C. freezer. The supernatant was cleared by centrifugation and by passing through 0.45 micron filtration unit. Cleared supernatant was loaded on a 20% sucrose cushion in ultracentrifuge tubes and tubes centrifuged at 30,000 rpm for 90 minutes at 4° C. in a Beckman Coulter Optima XPN90 ultracentrifuge. VLP pellets were re-suspended in PBS. Cell lysates and VLPs were resolved on 10% polyacrylamide gels, proteins transferred onto nitrocellulose membranes and the membranes probed by western blotting for the presence EBOV GP, SUDV GP and HIV-1 Gag using specific antibodies.

Production and characterization of ESGPGag VLPs: Once confirmed for ESGPGag VLP secretion, ESGPGag 293F cell cultures were scaled up, VLP pellets collected as described above and layered on a 20-60% sucrose gradient in ultracentrifuge tubes. Tubes were centrifuged at 35,000 rpm at 4° C. for 16 hours in an ultracentrifuge. After discarding the top 1.0 ml, twelve 900 µl fractions were collected in clean tubes. Buoyance density of each fraction was determined by using a refractometer. Fractions were probed by western blotting using anti-EBOV GP, anti-SUDV GP and anti-HIV-1 Gag specific antibodies. In separate experiments, VLPs collected after centrifugation on 20% sucrose cushion were analyzed by negative-stain electron microscopy for their shape and size. VLPs from eleven runs were pooled and quantified for EBOV GP and SUDV GP contents by quantitative western blotting using known amounts of recombinant EBOV GP protein and SUDV GP protein as the standards and specific antibodies.

Immunization of rabbits with ESGPGag VLPs: Raising of rabbit sera against ESGPGag VLPs was out-sourced to Cocalico Biologicals, Reamstown, PA. Briefly, two rabbits were primed intramuscularly with VLPs (equivalent to 10 µg of EBOV GP) mixed with 500 µg of CpG and 200 µg of Poly(I:C) adjuvants. This was followed by booster doses on day 21, 42 and 70 and animals were bled on day 77. Blood samples for serum were collected at pre-bleed and at days 49 and 77.

Binding antibodies: ELISA binding antibody titers against EBOV GP and SUDV GP were quantified by ELISA using purified recombinant GPs as the coating antigens. Briefly, ELISA plates were coated with 100 µl/well of 200 ng/ml of recombinant EBOV GP and SUDV GP. Wells were blocked and incubated for 2 hours at 37° C. with increasing dilutions of rabbit anti-ESGPGag VLP sera. Protein bound antibodies were detected by incubating the wells with optimally diluted horse radish peroxidase (HRP) bound anti-rabbit IgG detecting antibodies followed by the addition of TMB substrate, stopping the reaction with H2SO4 and measuring the optical density at 450 nm. Specificity of the antibodies was determined by analyzing their reactivity with recombinant EBOV GP or SUDV GP in a western blot system.

Neutralizing antibody titers: Neutralizing antibody titers were evaluated by using rHIV-1ΔEnv pseudovirions expressing EBOV or SUDV GP in a TZM-bl pseudovirus reporter cell method. rHIV-1ΔEnv pseudovirions expressing BDBV, TAFV or MARV GP were included to study the ability of anti-ESGPGag VLP sera to cross-neutralize other pathogenic Ebolaviruses as well as MARV. Pseudovirions were incubated with different dilutions of rabbit anti-ESGP-Gag VLP sera for one hour at 37° C. and then added onto confluent TZM-bl cells that express luciferase under the control of an HIV-1 Tat protein. 48 hours later luciferase activity was measured after the addition of the luciferase substrate and percentage neutralization calculated by comparing luciferase number in test wells with those in the wells that received the respective pseudovirion that was not incubated with any antibody/serum. Serum antibody titers giving 50% neutralization were calculated.

Results and Discussion

Development of ESGPGag 293F cells producing bivalent Ebola VLPs:

Transfection of 293F with pcDNA4 TO-HIV-1 Gag, pcDNA5 TO-EBOV GP and pcDNA5 TO-SUDV GP plasmids followed by their selection in antibiotic containing media over a four-week period resulted in the development of cells that upon induction with Dox produced HIV-1 Gag, EBOV GP and SUDV GP (FIG. 1) indicating that these genes have been stably integrated into the genome of these cells and can be turned on with the addition of Dox. Applicant labeled these stably transfected cells as ESGPGag 293F cells. Experiments were conducted to determine if EBOV GP, SUDV GP and HIV-1 Gag synthesized in ESGP-Gag 293F cells, after Dox induction, could spontaneously assemble into VLPs and be secreted into the medium. VLPs were isolated from the cell supernatant collected after 40 hours of Dox induction and were analyzed, along with the corresponding cell lysates, by western blotting for the presence EBOV GP, SUDV GP and HIV-1 Gag proteins using specific antibodies. As shown in FIG. 2, full length EBOV GP, SUDV GP and HIV-1 Gag were detected in both the cell lysate and in the VLPs indicating that EBOV GP, SUDV GP and HIV-1 Gag, synthesized upon induction of ESGPGag 293F cells with Dox spontaneously assemble into VLPs that are secreted out into the medium.

Characterization of ESGPGag VLPs:

Buoyance density analysis of ESGPGag VLP fractions collected over 20-60% sucrose density gradient showed that these particles range in density from 1.136-1.180 with the peak at 1.153 (FIG. 3). Electron microscopic analysis of the particles showed fine, spherical particles with a size of ~110 nm with EBOV GP and SUDV GP abundantly studded on the Gag matrix (FIG. 4). The particle density, shape and size observed in this study is in agreement with other VLPs and immature HIV-1 virions where Gag constitutes the spherical immature shell. Quantification of EBOV GP and SUDV GP contents in ESGPGag VLPs showed higher amount of EBOV GP as compared to SUDV GP with EBOV GP/SUDV GP ratio of 1:4.5.

Figure 5:
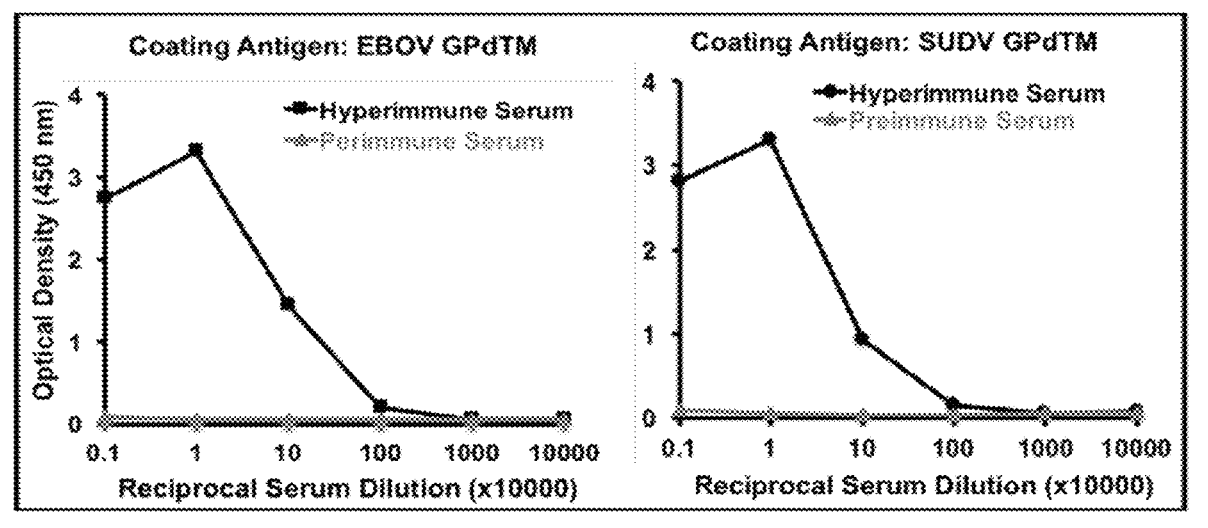

Immunogenicity of ESGPGag VLPs: Immunogenicity of ESGPGag VLPs was tested by their ability to induce high-titered binding anti-EBOV GP and SUDV GP antibody responses in rabbits. Rabbit serum samples collected one week after the last booster dose were heat inactivated and binding titers determined by analyzing the binding of antibodies present in increasing dilutions of the anti-sera to EBOV GP and SUDV GP coated ELISA plates. As shown in FIG. 5, ESGPGag VLPs were highly immunogenic in rabbits and anti-sera collected had anti-EBOV GP and SUDV GP end point antibody titers of $1:10^6$. Specificity of these antibodies was confirmed by their reactivity with recombinant EBOV GP and SUDV GP in a western blot system (data not shown). Functionality of the anti-ESGP Gag VLP serum was investigated by its ability to neutralize EBOV GP and SUDV GP containing HIV-1ΔEnv pseudovirions in a luciferase based neutralization assay using TZM-bl cells.

Figure 6:
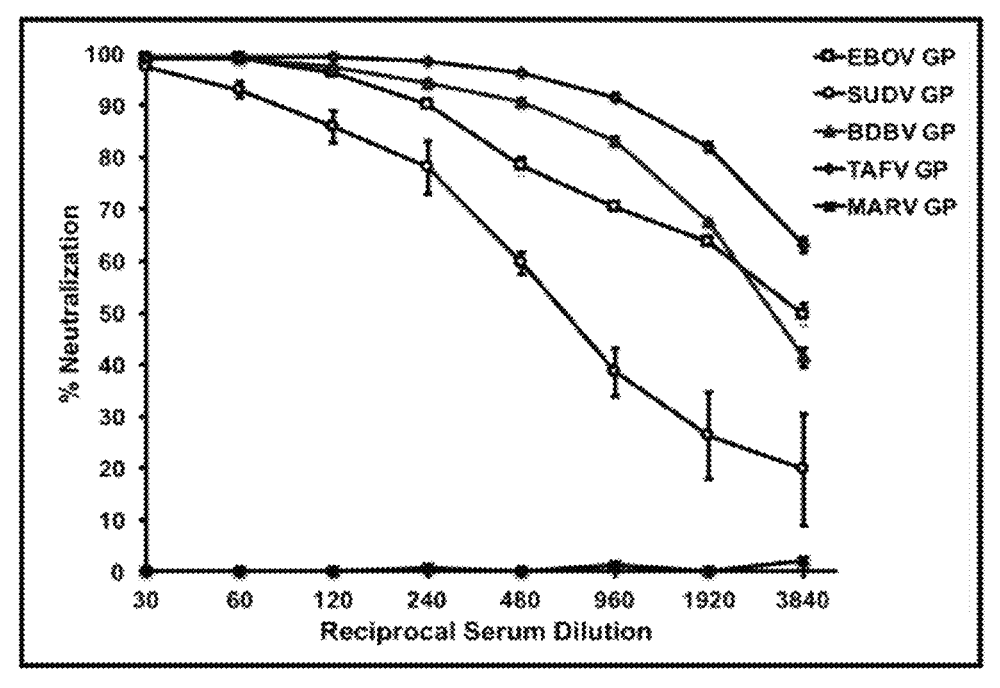

Luciferase gene in these cells is under the control of HIV-1 Tat protein. Additionally, BDBV GP and TAF GP containing HIV-1ΔEnv pseudovirions were included in these assays to study the ability of anti-ESGPGag VLP serum to cross-neutralize remaining two pathogenic members of this species. HIV-1ΔEnv pseudovirions with MARV GP were included as negative controls. FIG. 6 summarizes the results of neutralization experiments. Anti-ESGPGag VLP serum strongly neutralized EBOV, BDBV and TAFV with 50% neutralization titers of higher than 1:1920. 50% neutralization titer for SUDV was slightly lower (1:480). No neutralization was observed with MARV. Applicant has previously observed that rabbit anti-sera against monovalent EGPGag VLPs, that have EBOV GP on HIV-1 Gag core, strongly neutralized EBOV, BDBV and TAFV while much higher serum concentration is needed to neutralize SUDV (unpublished data). Inclusion of SUDV GP on bivalent Ebola VLPs significantly raised the neutralization titer of anti-bivalent VLP serum against the SUDV. This titer though was lower than that for the neutralization of other Ebolaviruses. This is likely because of the fact that compared to EBOV GP, there was relatively less SUDV GP on the bivalent Ebola VLPs. Enhancing SUDV GP content and bringing it to the level of EBOV GP might help in raising the anti-SUDV neutralization titer of anti-ESGPGag VLP serum.

Ebola VLP-based vaccine on Ebola VP40 core has been used in the past to immunize non-human primates that were subsequently challenged with lethal doses of Ebola virus. This vaccine induced humoral and cellular immune responses in animals that protected these animals against the Ebola challenge (12, 13). Because of the filamentous nature of the VP40 core, these VLPs were found to be unstable. Moreover, they were produced after the transient transfection of the cells and therefore are not readily amenable to large-scale production. VLPs may be produced, in an inducible fashion, from the stably transfected ESGPGag 293F cells. This production system can be easily adapted to large scale Ebola VLPs production, if needed. Being smaller in size and spherical in shape they are likely to be a stable and homogenous product.

REFERENCES

1. Messaoudi I, Amarasinghe G K, Basler C F. Filovirus pathogenesis and immune evasion: insights from Ebola virus and Marburg virus. Nat Rev Microbiol. 2015; 13(11):663-76.
2. Agnandji S T, Huttner A, Zinser M E, Njuguna P, Dahlke C, Fernandes J F, et al. Phase 1 Trials of rVSV Ebola Vaccine in Africa and Europe—Preliminary Report. N Engl J Med. 2015.
3. Huttner A, Dayer J A, Yerly S, Combescure C, Auderset F, Desmeules J, et al. The effect of dose on the safety and immunogenicity of the VSV Ebola candidate vaccine: a randomised double-blind, placebo-controlled phase 1/2 trial. Lancet Infect Dis. 2015; 15(10):1156-66.
4. Ledgerwood J E, DeZure A D, Stanley D A, Novik L, Enama M E, Berkowitz N M, et al. Chimpanzee Adenovirus Vector Ebola Vaccine—Preliminary Report. N Engl J Med. 2014.
5. Kibuuka H, Berkowitz N M, Millard M, Enama M E, Tindikahwa A, Sekiziyivu A B, et al. Safety and immunogenicity of Ebola virus and Marburg virus glycoprotein DNA vaccines assessed separately and concomitantly in healthy Ugandan adults: a phase 1b, randomised, double-blind, placebo-controlled clinical trial. Lancet. 2015; 385 (9977):1545-54.
6. Rampling T, Ewer K, Bowyer G, Wright D, Imoukhuede E B, Payne R, et al. A Monovalent Chimpanzee Adenovirus Ebola Vaccine—Preliminary Report. N Engl J Med. 2015.
7. Tapia M D, Sow S O, Lyke K E, Haidara F C, Diallo F, Doumbia M, et al. Use of ChAd3-EBO-Z Ebola virus vaccine in Malian and U S adults, and boosting of Malian adults with MVA-BN-Filo: a phase 1, single-blind, randomised trial, a phase 1b, open-label and double-blind, dose-escalation trial, and a nested, randomised, double-blind, placebo-controlled trial. Lancet Infect Dis. 2016; 16(1):31-42.
8. Zhu F C, Hou L H, Li J X, Wu S P, Liu P, Zhang G R, et al. Safety and immunogenicity of a novel recombinant adenovirus type-5 vector-based Ebola vaccine in healthy adults in China: preliminary report of a randomised, double-blind, placebo-controlled, phase 1 trial. Lancet. 2015; 385(9984):2272-9.
9. Henao-Restrepo A M, Longini I M, Egger M, Dean N E, Edmunds W J, Camacho A, et al. Efficacy and effectiveness of an rVSV-vectored vaccine expressing Ebola surface glycoprotein: interim results from the Guinea ring vaccination cluster-randomised trial. Lancet. 2015; 386 (9996):857-66.
10. Ledgerwood J E, DeZure A D, Stanley D A, Coates E E, Novik L, Enama M E, et al. Chimpanzee Adenovirus Vector Ebola Vaccine. N Engl J Med. 2017; 376(10):928-38.
11. Stanley D A, Honko A N, Asiedu C, Trefry J C, Lau-Kilby A W, Johnson J C, et al. Chimpanzee adenovirus vaccine generates acute and durable protective immunity against ebolavirus challenge. Nature medicine. 2014; 20(10):1126-9.
12. Warfield K L, Dye J M, Wells J B, Unfer R C, Holtsberg F W, Shulenin S, et al. Homologous and heterologous protection of nonhuman primates by Ebola and Sudan virus-like particles. PloS one. 2015; 10 (3):e0118881.
13. Warfield K L, Swenson D L, Olinger G G, Kalina W V, Aman M J, Bavari S. Ebola virus-like particle-based vaccine protects nonhuman primates against lethal Ebola virus challenge. The Journal of infectious diseases. 2007; 196 Suppl 2:S430-7.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making a bivalent VLP composition, comprising
   a. purifying from a cell line culture a VLP composition comprising a spherical retroviral Group-specific Antigen ("Gag") protein core and at least two Ebola glycoproteins, wherein said at least two Ebola glycoproteins are incorporated into the surface of said spherical Gag protein core;
   wherein said cell line is stably transfected with
      a first plasmid containing a gag sequence under the control of an inducible promoter,
      a second plasmid containing an Ebola glycoprotein sequence under the control of an inducible promoter, and
      a third plasmid containing an Ebola glycoprotein sequence under the control of an inducible promoter,
   wherein said second and third plasmid contain different Ebola glycoproteins.

2. The method of claim 1, wherein said stably transfected cell line produces said spherical Gag protein core, and wherein said at least two Ebola glycoproteins are located at the surface of said spherical Gag protein core.

3. The method of claim 1, wherein said stably transfected cell line produces said Gag protein core upon induction with doxycycline.

4. The method of claim 1, comprising purifying the VLP via ultracentrifugation.

5. The method of claim 1, wherein said first plasmid, second plasmid, and third plasmid are antibiotic resistant.

6. The method of claim 1, wherein said cell line is a human cell line modified to stably express Gag, EBOV GP, and SUDV GP under inducible promoters.

7. The method of claim 1, wherein said cell line is a 293F cell line.

8. The method of claim 1, wherein said cell line is a 293F 6/TR cell line.

9. A composition comprising a cell line comprising a first plasmid containing a sequence encoding for a gag protein under the control of an inducible promoter, a second plasmid containing a sequence encoding for a first Ebola glycoprotein under the control of an inducible promoter, and a third plasmid containing a sequence encoding for a second Ebola glycoprotein under the control of an inducible promoter.

10. The composition of claim 9, wherein said Ebola glycoprotein is Zaire (EBOV), and wherein said composition further comprises third plasmid containing a sequence encoding for a second Ebola glycoprotein under the control of an inducible promoter, wherein said second Ebola glycoprotein is SUDV.

11. The composition of claim 9, wherein said cell line is stably transfected with said plasmids.

12. The method of claim 1, comprising purifying the VLP via a sucrose cushion.

13. The method of claim 1, comprising purifying the VLP via a 20% sucrose cushion.

14. The method of claim 1, comprising purifying the VLP via cross-flow filtration followed by ultracentrifugation.

* * * * *

SEQUENCE LISTING

```
Sequence total quantity: 4
SEQ ID NO: 1            moltype = DNA  length = 1503
FEATURE                 Location/Qualifiers
misc_feature            1..1503
                        note = Codon-optimized HIV-1 Gag sequence
source                  1..1503
                        mol_type = other DNA
                        organism = synthetic construct
SEQUENCE: 1
atgggcgccc gcgccagcgt gctgagcggc ggcgagctgg accgctggga gaagatccgc  60
ctgcgccccg gcggcaagaa gaagtacaag ctgaagcaca tcgtgtgggc cagccgcgag  120
ctggagcgct tcgccgtgaa ccccggcctg ctggagacca gcgagggctg ccgccagatc  180
ctgggccagc tgcagcccag cctgcagacc ggcagcgagg agctgcgcag cctgtacaac  240
accgtggcca ccctgtactg cgtgcaccag cgcatcgaga tcaaggacac caaggaggcc  300
ctggacaaga tcgaggagga gcagaacaag agcaagaaga aggcccagca ggccgccgcc  360
gacaccggcc acagcaacca ggtgagccag aactacccca tcgtgcagaa catccagggc  420
cagatggtgc accaggccat cagcccccgc accctgaacg cctgggtgaa ggtggtggag  480
gagaaggcct tcagccccga ggtgatcccc atgttcagcg ccctgagcga gggcgccacc  540
ccccaggacc tgaacaccat gctgaacacc gtgggcggcc accaggccgc catgcagatg  600
ctgaaggaga ccatcaacga ggaggccgcc gagtgggacc gcgtgcaccc cgtgcacgcc  660
ggccccatcg cccccggcca gatgcgcgag ccccgcggca gcgacatcgc cggcaccacc  720
agcaccctgc aggagcagat cggctggatg accaacaacc cccccatccc cgtgggcgag  780
atctacaagc gctggatcat cctgggcctg aacaagatcg tgcgcatgta cagccccacc  840
agcatcctgg acatccgcca gggccccaag gagcccttcc gcgactacgt ggaccgcttc  900
tacaagaccc tgcgcgccga gcaggccagc caggaggtga agaactggat gaccgagacc  960
ctgctggtgc agaacgccaa ccccgactgc aagaccatcc tgaaggccct gggccccgcc  1020
gccaccctgg aggagatgat gaccgcctgc cagggcgtgg gcggccccgg ccacaaggcc  1080
cgcgtgctgg ccgaggccat gagccaggtg accaacagcg ccaccatcat gatgcagcgc  1140
ggcaacttcc gcaaccagcg caagatcgtg aagtgcttca actgcggcaa ggagggccac  1200
accgcccgca actgccgcgc cccccgcaag aagggctgct ggaagtgcgg caaggagggc  1260
caccagatga aggactgcac cgagcgacag gctaattttt tagggaagat ctggccttcc  1320
cacaagggaa ggccagggaa ttttcttcag agcagaccag agccaacagc cccaccagaa  1380
gagagcttca ggtttgggga agagacaaca actccctctc agaagcagga gccgatagac  1440
aaggaactgt atcctttagc ttccctcaga tcactctttg gcagcgaccc ctcgtcacaa  1500
taa                                                                1503

SEQ ID NO: 2            moltype = DNA  length = 2035
FEATURE                 Location/Qualifiers
misc_feature            1..2035
                        note = EBOV GP
source                  1..2035
                        mol_type = other DNA
                        organism = synthetic construct
SEQUENCE: 2
atgggcgtca ctggtattct gcagctgccc cgagataggt tcaagcggac ttccttcttc  60
ctgtgggtca tcattctgtt tcagcggact ttcagcatcc ctctgggcgt gattcacaac  120
tcaaccctgc aggtgagcga cgtggataag ctggtctgtc gcgacaaact gagctccacc  180
aatcagctgc gatccgtggg actgaatctg gagggtaacg gagtggcaac tgatgtccca  240
agcgccacca aacggtgggg gtttaggtcc ggtgtgcccc ctaaggtggt caactacgag  300
gctggcgaat gggcagagaa ttgctataac ctggaaatca agaaacctga cggcagcgag  360
tgtctgccag cagctcctga tggcattagg ggattcccta ggtgcagata cgtgcacaaa  420
gtctctggaa ccgggccatg tgccggagac ttcgcttttc ataaggaagg ggcattcttt  480
ctgtacgatc gactggcctc caccgtgatc tatcggggaa ccacattcgc tgagggggtg  540
gtcgcatttc tgattctgcc ccaggctaag aaagacttct tttctagtca cccactgcgc  600
gaacccgtga acgcaaccga ggacccctca agcggctact atagtactac catccgatac  660
caggccacag gtttcggcac aaatgagact gaatacctgt ttgaagtgga caacctgact  720
tatgtccagc tggagagcag gttcacccct cagtttctgc tgcagctgaa cgaaaccatc  780
tatacaagcg gcaagcggag caatacaact ggcaagctga tttggaaagt gaacccagag  840
atcgatacca caattggcga atgggccttt tgggagacaa agaaaaatct gactcgcaaa  900
atccgatctg aggaactgag tttcaccgtg gtctccaatg gtgctaagaa cattagtggc  960
cagtcaccag cacgcacatc ctctgacccc gggactaata ctaccacaga agatcacaag  1020
atcatggcat ctgagaacag ttcagccatg gtgcaggtcc acagtcaggg acgagaggca  1080
gccgtgtcac atctgactac cctggccact atctctacca gtccacagtc tctgacaact  1140
aaacctggac cagacaatag tacacataac actcccgtgt acaagctgga tattagtgaa  1200
gccacacagg tcgagcagca ccatcggagg actgacaacg atagcaccgc ttccgacaca  1260
```

```
ccatcagcaa ccacagctgc aggcccaccc aaagctgaga ataccaacac atcaaagagc 1320
actgacttcc tggaccccgc cactaccaca tccccacaga atcactctga gacagctgga 1380
aacaataaca cccaccatca ggacacaggg gaggaatctg ccagctccgg gaagctgggt 1440
ctgatcacta acaccattgc cggcgtggct ggactgatca ctggcggaag acgcacccga 1500
cgggaagcaa ttgtgaatgc ccagcctaag tgcaatccaa acctgcacta ctggactacc 1560
caggacgagg gagcagctat cggactggct tggattccct acttcgggcc tgcagccgaa 1620
ggtatctata ttgagggcct gatgcataat caggatgggc tgatctgtgg tctgcgccag 1680
ctggccaacg aaacaactca ggctctgcag ctgttcctga gagcaaccac agagctgcgc 1740
acctttcta tcctgaacag gaaggccatt gacttcctgc tgcagagatg gggaggtaca 1800
tgccacatcc tgggaccaga ctgctgtatt gagcctcatg attggactaa gaatatccat 1860
gacaaaattg atcagatcat tcacgacttt gtggataaga cactgcctga tcagggtgac 1920
aatgataact ggtggactgg atggcgacag tggattcccg caggaattgg ggtgaccggc 1980
gtcatcattg cagtgatcgc cctgttttgc atttgtaaat tcgtgttttg agaat       2035

SEQ ID NO: 3              moltype = AA   length = 676
FEATURE                   Location/Qualifiers
source                    1..676
                          mol_type = protein
                          organism = Zaire ebolavirus
SEQUENCE: 3
MGVTGILQLP RDRFKRTSFF LWVIILFQRT FSIPLGVIHN STLQVSDVDK LVCRDKLSST  60
NQLRSVGLNL EGNGVATDVP SATKRWGFRS GVPPKVVNYE AGEWAENCYN LEIKKPDGSE 120
CLPAAPDGIR GFPRCRYVHK VSGTGPCAGD FAFHKEGAFF LYDRLASTVI YRGTTFAEGV 180
VAFLILPQAK KDFFSSHPLR EPVNATEDPS SGYYSTTIRY QATGFGTNET EYLFEVDNLT 240
YVQLESRFTP QFLLQLNETI YTSGKRSNTT GKLIWKVNPE IDTTIGEWAF WETKKNLTRK 300
IRSEELSFTV VSNGAKNISG QSPARTSSDP GTNTTTEDHK IMASENSSAM VQVHSQGREA 360
AVSHLTTLAT ISTSPQSLTT KPGPDNSTHN TPVYKLDISE ATQVEQHHRR TDNDSTASDT 420
PSATTAAGPP KAENTNTSKS TDFLDPATTT SPQNHSETAG NNNTHHQDTG EESASSGKLG 480
LITNTIAGVA GLITGGRRTR REAIVNAQPK CNPNLHYWTT QDEGAAIGLA WIPYFGPAAE 540
GIYIEGLMHN QDGLICGLRQ LANETTQALQ LFLRATTELR TFSILNRKAI DFLLQRWGGT 600
CHILGPDCCI EPHDWTKNIT DKIDQIIHDF VDKTLPDQGD NDNWWTGWRQ WIPAGIGVTG 660
VIIAVIALFC ICKFVF                                                 676

SEQ ID NO: 4              moltype = AA   length = 676
FEATURE                   Location/Qualifiers
source                    1..676
                          mol_type = protein
                          organism = Sudan ebolavirus
SEQUENCE: 4
MGGLSLLQLP RDKFRKSSFF VWVIILFQKA FSMPLGVVTN STLEVTEIDQ LVCKDHLAST  60
DQLKSVGLNL EGSGVSTDIP SATKRWGFRS GVPPKVVSYE AGEWAENCYN LEIKKPDGSE 120
CLPPPPDGVR GFPRCRYVHK AQGTGPCPGD YAFHKDGAFF LYDRLASTVI YRGVNFAEGV 180
IAFLILAKPK ETFLQSPPIR EAVNYTENTS SYYATSYLEY EIENFGAQHS TTLFKIDNNT 240
FVRLDRPHTP QFLFQLNDTI HLHQQLSNTT GRLIWTLDAN INADIGEWAF WENKKNLSEQ 300
LRGEELSFEA LSLNETEDDD AASSRITKGR ISDRATRKYS DLVPKNSPGM VPLHIPEGET 360
TLPSQNSTEG RRVGVNTQET ITETAATIIG TNGNHMQIST IGIRPSSSQI PSSSPTTAPS 420
PEAQTPTTHT SGPSVMATEE PTTPPGSSPG PTTEAPTLTT PENITTAVKT VLPQESTSNG 480
LITSTVTGIL GSLGLRKRSR RQTNTKATGK CNPNLHYWTA QEQHNAAGIA WIPYFGPGAE 540
GIYTEGLMHN QNALVCGLRQ LANETTQALQ LFLRATTELR TYTILNRKAI DFLLRRWGGT 600
CRILGPDCCI EPHDWTKNIT DKINQIIHDF IDNPLPNQDN DDNWWTGWRQ WIPAGIGITG 660
IIIAIIALLC VCKLLC                                                 676
```